(12) United States Patent
Hunt et al.

(10) Patent No.: US 12,016,994 B2
(45) Date of Patent: Jun. 25, 2024

(54) SENSOR ENABLED NEGATIVE PRESSURE WOUND MONITORING APPARATUS WITH DIFFERENT IMPEDANCES INKS

(71) Applicant: Smith & Nephew PLC, Watford (GB)

(72) Inventors: Allan Kenneth Frazer Grugeon Hunt, Beverley (GB); Felix Clarence Quintanar, Hull (GB)

(73) Assignee: Smith & Nephew PLC, Watford (GB)

( * ) Notice: Subject to any disclaimer, the term of this patent is extended or adjusted under 35 U.S.C. 154(b) by 0 days.

(21) Appl. No.: 17/766,887

(22) PCT Filed: Oct. 1, 2020

(86) PCT No.: PCT/EP2020/077464
§ 371 (c)(1),
(2) Date: Apr. 6, 2022

(87) PCT Pub. No.: WO2021/069286
PCT Pub. Date: Apr. 15, 2021

(65) Prior Publication Data
US 2024/0091430 A1 Mar. 21, 2024

(30) Foreign Application Priority Data
Oct. 7, 2019 (GB) ..................................... 1914443

(51) Int. Cl.
*A61M 1/00* (2006.01)
(52) U.S. Cl.
CPC ....... *A61M 1/95* (2021.05); *A61M 2205/3317* (2013.01)
(58) Field of Classification Search
CPC .................. A61M 1/95; A61M 2205/3317

USPC ........................................................ 604/313
See application file for complete search history.

(56) References Cited

U.S. PATENT DOCUMENTS

| 3,896,802 A | | 7/1975 | Williams |
| 4,334,530 A | | 6/1982 | Hassell |
| 5,036,859 A | * | 8/1991 | Brown ...................... A61F 5/48 340/573.5 |

(Continued)

FOREIGN PATENT DOCUMENTS

| CA | 2844534 A1 * | 2/2013 | ............. A61F 13/42 |
| CN | 105232229 A | 1/2016 | |

(Continued)

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).

(Continued)

*Primary Examiner* — Andrew J Mensh
(74) *Attorney, Agent, or Firm* — Knobbe, Martens, Olson & Bear, LLP

(57) ABSTRACT

A sensor sheet of a wound monitoring and/or therapy apparatus can include one or more electrical connections. The electrical connections can include multiple conductive inks having different impedances. A track of first conductive ink having a first impedance can be coupled to an electrical connector of an electronic component. A track of second conductive ink having a second impedance can be coupled to the track of first conductive ink.

20 Claims, 10 Drawing Sheets

(56) References Cited

U.S. PATENT DOCUMENTS

| | | |
|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,480,641 B2 | 7/2013 | Jacobs |
| 8,525,340 B2 | 9/2013 | Eckhardt et al. |
| 8,579,872 B2 | 11/2013 | Coulthard et al. |
| 8,644,911 B1 | 2/2014 | Panasyuk et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,204,806 B2 | 12/2015 | Stivoric et al. |
| 9,220,455 B2 | 12/2015 | Sarrafzadeh et al. |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,380,698 B1 | 6/2016 | Li et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,844,145 B2 | 12/2017 | Hsu |
| 9,907,103 B2 | 2/2018 | Chen et al. |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,166,387 B2 | 1/2019 | Bergelin et al. |
| 10,182,740 B2 | 1/2019 | Tonar et al. |
| 10,201,644 B2 | 2/2019 | Haggstrom et al. |
| 10,206,604 B2 | 2/2019 | Bergelin et al. |
| 10,209,213 B2 | 2/2019 | Kang et al. |
| 10,285,620 B2 | 5/2019 | Jung et al. |
| 10,288,590 B2 | 5/2019 | Hammond et al. |
| 10,321,862 B2 | 6/2019 | Dalene et al. |
| 10,463,773 B2 | 11/2019 | Haggstrom et al. |
| 10,687,984 B2 | 6/2020 | Rovaniemi |
| 10,702,153 B2 | 7/2020 | Shamim et al. |
| 10,716,490 B2 | 7/2020 | Connolly |
| 10,857,038 B2 | 12/2020 | Zamierowski et al. |
| 11,026,847 B2 | 6/2021 | Piotrowski et al. |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0176675 A1* | 9/2004 | Rice ............... A61B 5/7278 600/407 |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0270774 A1* | 11/2007 | Bergman ............... G16H 40/60 604/361 |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |

(56) References Cited

U.S. PATENT DOCUMENTS

| | | |
|---|---|---|
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0165717 A1 | 6/2012 | Al Khaburi |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0211208 A1 | 8/2013 | Varadan et al. |
| 2013/0261409 A1 | 10/2013 | Pathak et al. |
| 2013/0271278 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0003579 A1 | 1/2018 | Esposito et al. |
| 2018/0008177 A1 | 1/2018 | Shimuta et al. |
| 2018/0049923 A1* | 2/2018 | Chen ................. A61F 13/01042 |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0266976 A1* | 9/2018 | Naiknaware ......... G01N 27/048 |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |

(56) References Cited

U.S. PATENT DOCUMENTS

| | | |
|---|---|---|
| 2019/0134280 A1 | 5/2019 | Toth |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0060541 A1* | 2/2020 | Andrade ............ A61B 5/14517 |
| 2020/0078482 A1 | 3/2020 | Yoon et al. |
| 2020/0078499 A1 | 3/2020 | Gadde et al. |
| 2020/0100711 A1 | 4/2020 | Choudhury et al. |
| 2020/0147407 A1 | 5/2020 | Efremkin |
| 2020/0281512 A1 | 9/2020 | Grubb et al. |
| 2020/0281513 A1 | 9/2020 | Grubb et al. |
| 2020/0281529 A1 | 9/2020 | Grubb et al. |
| 2020/0289346 A1 | 9/2020 | Hansen et al. |
| 2020/0330258 A1 | 10/2020 | Hansen et al. |
| 2020/0360547 A1 | 11/2020 | Smith et al. |
| 2021/0137446 A1 | 5/2021 | Brownhill et al. |
| 2021/0145359 A1 | 5/2021 | Hunt et al. |
| 2022/0031231 A1* | 2/2022 | Hunt ........................ A61M 1/95 |
| 2022/0079509 A1 | 3/2022 | Gellman et al. |

FOREIGN PATENT DOCUMENTS

| | | |
|---|---|---|
| CN | 105395184 A | 3/2016 |
| CN | 106102322 A | 11/2016 |
| CN | 109350362 A | 2/2019 |
| DE | 102012211015 A1 | 1/2014 |
| DE | 102013013013 A1 | 2/2015 |
| EP | 2454990 A2 | 5/2012 |
| EP | 2565630 A1 | 3/2013 |
| EP | 3231478 A1 | 10/2017 |
| EP | 3409190 A1 | 12/2018 |
| EP | 3499510 A1 | 6/2019 |
| EP | 3563761 A1 | 11/2019 |
| GB | 2316171 A | 2/1998 |
| GB | 2563602 A | 12/2018 |
| JP | 2006019336 A | 1/2006 |
| JP | 2009225863 A | 10/2009 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-0021433 A1 | 4/2000 |
| WO | WO-0043046 A2 | 7/2000 |
| WO | WO-03067229 A1 | 8/2003 |
| WO | WO-2006041997 A2 | 4/2006 |
| WO | WO-2007030379 A2 | 3/2007 |
| WO | WO-2008006150 A1 | 1/2008 |
| WO | WO-2008010604 A1 | 1/2008 |
| WO | WO-2009052607 A1 | 4/2009 |
| WO | WO-2009103165 A1 * | 8/2009 ........... A61B 5/0059 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011113070 A1 | 9/2011 |
| WO | WO-2011123848 A1 | 10/2011 |
| WO | WO-2012141999 A1 | 10/2012 |
| WO | WO-2013026999 A1 | 2/2013 |
| WO | WO-2013044226 A2 | 3/2013 |
| WO | WO-2014036577 A1 | 3/2014 |
| WO | WO-2015112095 A1 | 7/2015 |
| WO | WO-2015127218 A1 | 8/2015 |
| WO | WO-2015168720 A1 | 11/2015 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016110564 A1 | 7/2016 |
| WO | WO-2016187136 A1 | 11/2016 |
| WO | WO-2016205872 A1 | 12/2016 |
| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017205728 A1 | 11/2017 |
| WO | WO-2017214188 A1 | 12/2017 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |
| WO | WO-2018144946 A1 | 8/2018 |
| WO | WO-2018185138 A1 | 10/2018 |
| WO | WO-2018189265 A1 | 10/2018 |
| WO | WO-2018209090 A1 | 11/2018 |
| WO | WO-2018211458 A1 | 11/2018 |
| WO | WO-2018234443 A1 | 12/2018 |
| WO | WO-2019020550 A2 | 1/2019 |
| WO | WO-2019020551 A1 | 1/2019 |
| WO | WO-2019020666 A1 | 1/2019 |
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |
| WO | WO-2019063481 A1 | 4/2019 |
| WO | WO-2019063488 A2 | 4/2019 |
| WO | WO-2019067264 A1 | 4/2019 |
| WO | WO-2019072531 A1 | 4/2019 |
| WO | WO-2019076967 A2 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |
| WO | WO-2019238197 A1 | 12/2019 |
| WO | WO-2019238198 A1 | 12/2019 |
| WO | WO-2020043806 A1 | 3/2020 |
| WO | WO-2020139541 A1 | 7/2020 |
| WO | WO-2020157103 A1 | 8/2020 |
| WO | WO-2020159677 A1 | 8/2020 |
| WO | WO-2020167547 A1 | 8/2020 |
| WO | WO-2020242876 A1 | 12/2020 |
| WO | WO-2021059209 A1 | 4/2021 |

OTHER PUBLICATIONS

Bandodkar A.J., et al., "Battery-Free, Skin-Interfaced Microfluidic/Electronic Systems for Simultaneous Electrochemical, Colorimetric and Volumetric Analysis of Sweat," Science Advances, vol. 5 (1), Jan. 18, 2019, retrieved from http://advances.sciencemag.org/content/5/1/eaav3294, 16 pages.

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

(56) References Cited

OTHER PUBLICATIONS

Geng Y., et al., "A Hybrid Low Power Biopatch for Body Surface Potential Measurement," IEEE Journal of Biomedical and Health Informatics, vol. 17, No. 3, May 1, 2013, pp. 591-599.

George J., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

International Search Report and Written Opinion for Application No. PCT/EP2020/077464, mailed on Jan. 13, 2021, 14 pages.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for μTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mehmood N., et al., "Applications of Modern Sensors and Wireless Technology in Effective Wound Management: Modern Sensors and Wireless Technology," Journal of Biomedical Materials Research Part B, vol. 102, May 1, 2014, XP055739544, pp. 885-895.

Mostafalu P., et al., "Wireless Flexible Smart Bandage for Continuous Monitoring of Wound Oxygenation," IEEE Transactions on Biomedical Circuits and Systems, vol. 9 (5), Oct. 1, 2015, XP055526132, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Pang Q., et al., "Smart Flexible Electronics-Integrated Wound Dressing for Real-Time Monitoring and On-Demand Treatment of Infected Wounds," Advanced Science, vol. 7, No. 6, Mar. 2020, 1902673, XP055739532, 10 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

* cited by examiner

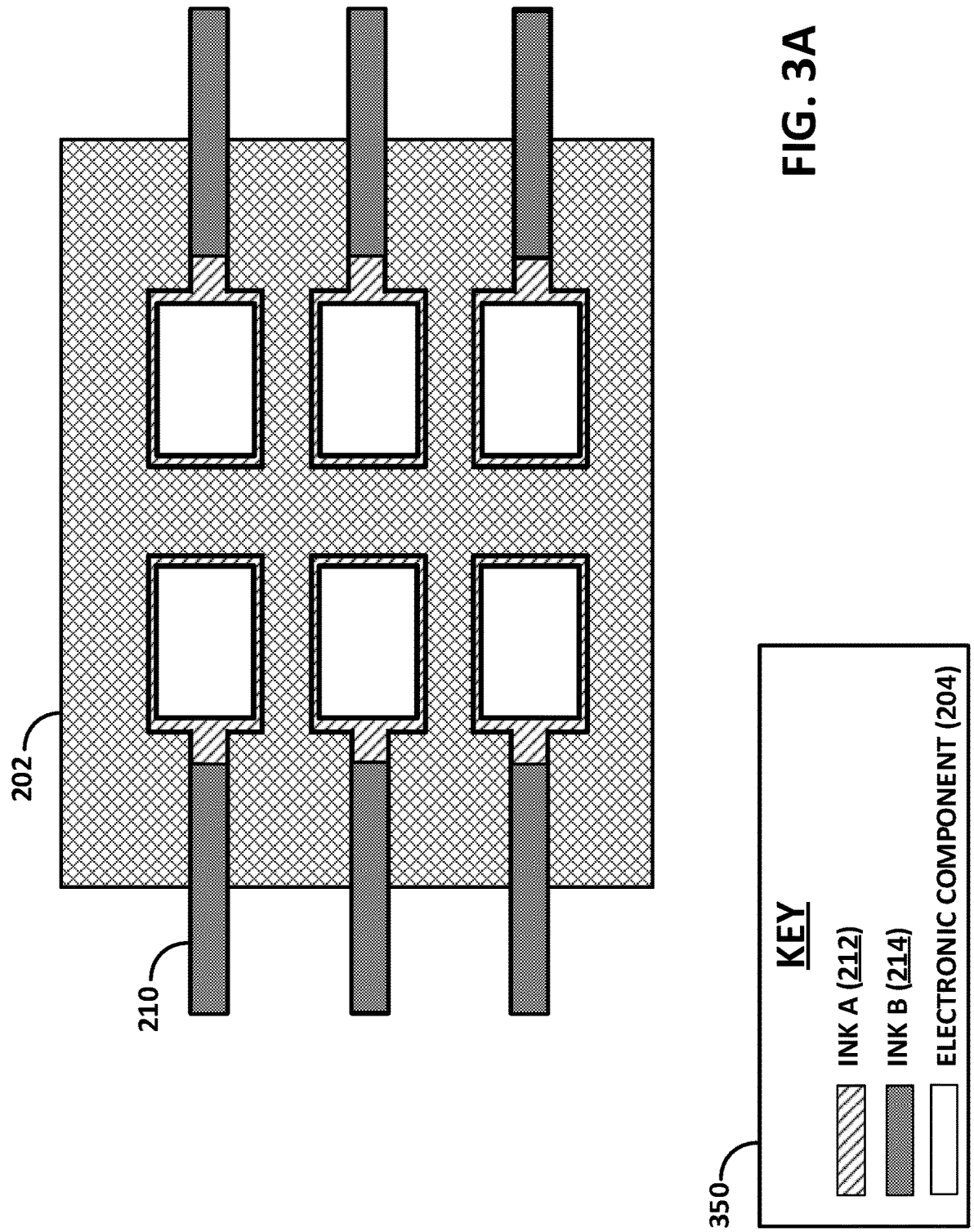

SENSOR ENABLED NEGATIVE PRESSURE WOUND MONITORING APPARATUS WITH DIFFERENT IMPEDANCES INKS

CROSS-REFERENCE TO RELATED APPLICATIONS

This application is a U.S. national stage application of International Patent Application No. PCT/EP2020/077464, filed Oct. 1, 2020, which claims priority to U.K. Provisional Application No. 1914443. 5 filed on Oct. 7, 2019, the disclosure of which is hereby incorporated by reference in its entirety.

BACKGROUND

Technical Field

Embodiments of the present disclosure relate to sensor integrated substrates, which can be incorporated into wound dressings and systems, and in particular to design rules for such substrates.

Description of the Related Art

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Such wound monitoring and/or treatment systems present unique problems due to being in contact with tissue. In addition, a wound should be allowed to heal without impediment. At the same time, care must be taken to ensure that such systems are reliable and safe for use on human or animal tissue.

Therefore, there is a need for improved wound monitoring and/or treatment systems.

SUMMARY

In some cases, a sensor sheet of a wound monitoring and/or therapy apparatus (such as a wound dressing) includes a plurality of electronic components. The plurality of electronic components can include at least a first electronic component. The first electronic component can include a first electrical connector configured to electrically connect the first electronic component. The wound monitoring and/or therapy apparatus can include a substantially flexible substrate. The substantially flexible substrate can include a first, wound-facing side supporting the plurality of electronic components and a second side opposite the first side. The wound monitoring and/or therapy apparatus can include a track of first conductive ink with a first impedance. The first conductive ink can reside on the substantially flexible substrate. The track of the first conductive ink can be electrically coupled to the first electrical connector of the first electronic component. The wound monitoring and/or therapy apparatus can include a track of second conductive ink with a second impedance different from the first impedance. The second conductive ink can reside on the substantially flexible substrate. The track of the second conductive ink can be electrically coupled to the track of first conductive ink.

The sensor sheet of the preceding paragraph may also include any combination of the following features described in this paragraph, among other features described herein. A soldering paste can be electrically coupled between the first electrical connector and the first electronic component. The soldering paste electrically can couples the first electrical connector and the first electronic component. The first conductive ink can bond better (e.g., form a superior electrical connection) with the soldering paste than the second conductive ink. The track of second conductive ink can be electrically coupled to the first electronic component via the track of first conductive ink. The track of the first conductive ink can be a first track of the first conductive ink. The sensor sheet can include a second track of the first conductive ink coupled to the track of the second conductive ink. The second track of the first conductive ink can be electrically coupled to the first track of the first conductive ink via the track of the second conductive ink. The track of the first conductive ink can be a first track of the first conductive ink. The plurality of electronic components can include a second electronic component that includes a second electrical connector. The sensor sheet can include a second track of the first conductive ink coupled to the second electrical connector of the second electronic component.

The sensor sheet of any of the preceding two paragraphs may also include any combination of the following features described in this paragraph, among other features described herein. The track of the second conductive ink can be coupled to the second track of the first conductive ink. The first electronic component can be electrically coupled to the second electronic component via the first track of the first conductive ink, the track of the second conductive ink, and the second track of the first conductive ink. The track of the second conductive ink can be a first track of the second conductive ink. The sensor sheet can include a second track of the second conductive ink coupled to the second track of the first conductive ink. The first electronic component can include at least one of a sensor, an amplifier, a capacitor, a resistor, an inductor, a controller, a processor, a diode, or a connector. At least one of the first conductive ink or the second conductive ink can include silver ink.

The sensor sheet of any of the preceding three paragraphs may also include any combination of the following features described in this paragraph, among other features described herein. An impedance variance due to stretching of the second conductive ink can be smaller than an impedance variance due to stretching of the first conductive ink. The first conductive ink can have a first width, and the second conductive ink can have a second width that is larger than the first width. A thermal conductivity of the first conductive ink can be higher than a thermal conductivity of the second conductive ink. At least one of the first conductive ink or the second conductive ink can include an electrical textile. The electrical textile can be cotton.

The sensor sheet of any of the preceding four paragraphs may also include any combination of the following features described in this paragraph, among other features described herein. The first conductive ink can include a fiber. The fiber can reduce an impedance variance due to stretching of the first conductive ink. The first impedance can be greater than the second impedance. The first conductive ink can be more conductive than the second conductive ink. At least a portion of the track of the second conductive ink can overlap with at least a portion of the track of first conductive ink. The track of the second conductive ink can be electrically coupled to the track of first conductive ink using conductive glue. The track of the second conductive ink can be electrically coupled to the track of first conductive ink using conductive tape. The first conductive ink can include a first amount of silver. The second conductive ink can include a second amount of silver that is different from the first amount.

Any of the features of any of the methods described herein can be used with any of the features of any of the other methods described herein.

BRIEF DESCRIPTION OF THE DRAWINGS

Embodiments of the present disclosure will now be described hereinafter, by way of example only, with reference to the accompanying drawings in which:

FIGS. 3A-3C illustrate substrates that support a plurality of electronic components and a plurality of electrical connections electrically connecting one or more of the electronic components.

DETAILED DESCRIPTION

Figure 1A:
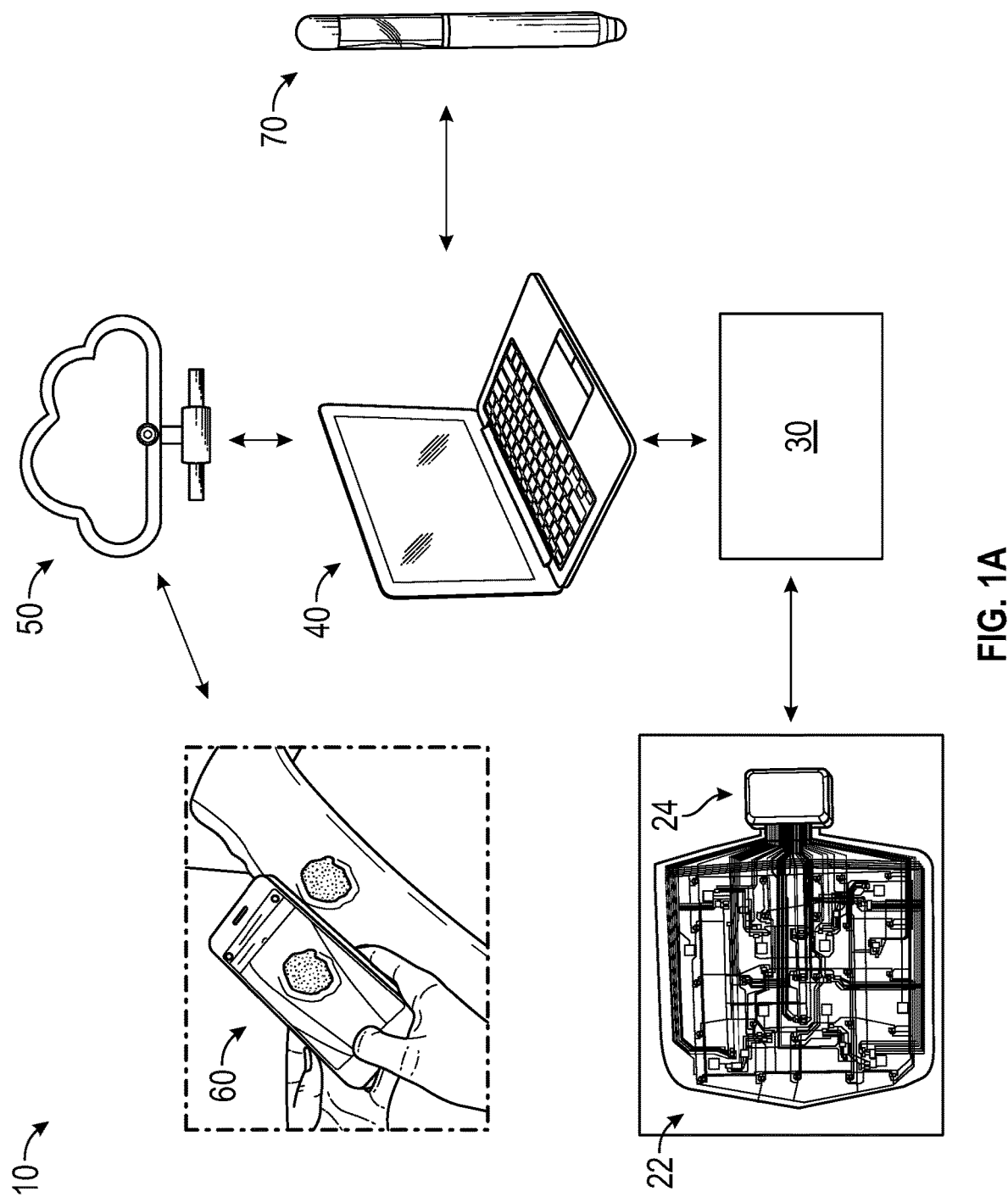
FIG. 1A illustrates a wound monitoring or therapy system.

Embodiments disclosed herein relate to apparatuses and methods of at least one of monitoring or treating biological tissue with sensor-enabled substrates. The systems and methods disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some systems and methods disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain cases, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor systems and methods disclosed herein may be used in combination with clothing. Non-limiting examples of clothing for use with the sensor systems and methods disclosed herein include shirts, pants, trousers, dresses, undergarments, outer-garments, gloves, shoes, hats, and other suitable garments. In certain cases, the sensor systems and methods disclosed herein may be welded into or laminated into/onto the particular garments. The sensor systems and methods may be printed directly onto the garment and/or embedded into the fabric. Breathable and printable materials such as microporous membranes may also be suitable.

Sensor systems and methods disclosed herein may be incorporated into cushioning or bed padding, such as within a hospital bed, to monitor patient characteristics, such as any characteristic disclosed herein. In certain cases, a disposable film containing such sensors could be placed over the hospital bedding and removed/replaced as needed.

In some implementations, the sensor systems and methods disclosed herein may incorporate energy harvesting, such that the sensor systems and methods are self-sustaining. For example, energy may be harvested from thermal energy sources, kinetic energy sources, chemical gradients, or any suitable energy source.

The sensor systems and methods disclosed herein may be utilized in rehabilitation devices and treatments, including sports medicine. For example, the sensor systems and methods disclosed herein may be used in braces, sleeves, wraps, supports, and other suitable items. Similarly, the sensor systems and methods disclosed herein may be incorporated into sporting equipment, such as helmets, sleeves, and/or pads. For example, such sensor systems and methods may be incorporated into a protective helmet to monitor characteristics such as acceleration, which may be useful in concussion diagnosis.

The sensor systems and methods disclosed herein may be used in coordination with surgical devices, for example, the NAVIO surgical system by Smith & Nephew Inc. In some implementations, the sensor systems and methods disclosed herein may be in communication with such surgical devices to guide placement of the surgical devices. In some implementations, the sensor systems and methods disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor systems and methods disclosed herein may be incorporated into the border or interior of a drape to create fencing to limit/control the surgical theater.

Sensor systems and methods disclosed herein may also be utilized for pre-surgical assessment. For example, such sensor systems and methods may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor systems and methods such as those disclosed herein may be used to evaluate the presence of microbial infection and provide an indication for the use of antimicrobials. Further, sensor systems and methods disclosed herein may collect further information in deeper tissue, such as identifying pressure ulcer damage and/or the fatty tissue levels.

The sensor systems and methods disclosed herein may be utilized in cardiovascular monitoring. For example, such sensor systems and methods may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor systems and methods disclosed herein may be utilized for neurophysiological applications, such as monitoring electrical activity of neurons.

The sensor systems and methods disclosed herein may be incorporated into implantable devices, such as implantable orthopedic implants, including flexible implants. Such sensor systems and methods may be configured to collect information regarding the implant site and transmit this information to an external source. In some cases, an internal source may also provide power for such an implant.

The sensor systems and methods disclosed herein may also be utilized for monitoring biochemical activity on the surface of the skin or below the surface of the skin, such as lactose buildup in muscle or sweat production on the surface of the skin. In some cases, other characteristics may be monitored, such as glucose concentration, urine concentration, tissue pressure, skin temperature, skin surface conductivity, skin surface resistivity, skin hydration, skin maceration, and/or skin ripping.

Sensor systems and methods disclosed herein may be incorporated into Ear, Nose, and Throat (ENT) applications. For example, such sensor systems and methods may be utilized to monitor recovery from ENT-related surgery, such as wound monitoring within the sinus passage.

Sensor systems and methods disclosed herein may encompass sensor printing technology with encapsulation, such as encapsulation with a polymer film. Such a film may be constructed using any polymer described herein, such as polyurethane. Encapsulation may provide waterproofing of the electronics and protection from local tissue, local fluids, and other sources of potential damage.

In certain cases, the sensors disclosed herein may be incorporated into an organ protection layer. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some cases, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor systems and methods disclosed herein may be incorporated into treatments for wounds (disclosed in greater detail below) or in a variety of other applications. Non-limiting examples of additional applications for the sensor systems and methods disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some systems and methods disclosed herein relate to wound therapy for a human or animal body. Therefore, any reference to a wound herein can refer to a wound on a human or animal body, and any reference to a body herein can refer to a human or animal body. The disclosed systems and methods may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some cases, the wound dressing can be provided to be utilized without reduced pressure.

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some disclosure relates to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure (TNP) and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some cases, a wound dressing comprises one or more absorbent layer(s). The absorbent layer may be a foam or a superabsorbent.

In some cases, the disclosed technology may be used in conjunction with a non-negative pressure dressing. A non-negative pressure wound dressing suitable for providing protection at a wound site may comprise an absorbent layer for absorbing wound exudate and an obscuring element for at least partially obscuring a view of wound exudate absorbed by the absorbent layer in use. The obscuring element may be partially translucent. The obscuring element may be a masking layer.

In some cases, the non-negative pressure wound dressing as disclosed herein comprises the wound contact layer and the absorbent layer overlies the wound contact layer. The wound contact layer can carry an adhesive portion for forming a substantially fluid tight seal over the wound.

In some cases, the wound dressing as disclosed herein further comprises layer of a superabsorbent fiber, or a viscose fiber or a polyester fiber.

In some cases, the wound dressing as disclosed herein further comprises a backing layer. The backing layer may be a transparent or opaque film. Typically the backing layer comprises a polyurethane film (typically a transparent polyurethane film).

In some cases, the foam may be an open cell foam, or closed cell foam, typically an open cell foam. The foam can be hydrophilic.

The wound dressing may comprise a transmission layer and the layer can be foam. The transmission layer may be a polyurethane foam laminated to a polyurethane film.

The non-negative pressure wound dressing may be a compression bandage. Compression bandages are known for use in the treatment of oedema and other venous and lymphatic disorders, e.g., of the lower limbs. The compression bandage may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb.

Negative Pressure Wound Therapy

In some cases, treatment of wounds can be performed using negative pressure wound therapy. It will be understood that systems and methods of the present disclosure can be generally applicable for use in TNP systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some cases, local ambient atmospheric pressure is used as a reference point, and such local atmospheric pressure may not necessarily be, for example, 760 mmHg.

In some wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via some of the wound closure devices. In some cases, negative pressure may be varied over time for example using a sinusoidal wave, square wave, or in synchronization with one or more physiological indices (such as, heartbeat).

Any of the systems and methods disclosed herein can be used in combination with any of the features disclosed in one or more of WO2010/061225, US2016/114074, US2006/0142560, and U.S. Pat. No. 5,703,225, which describe absorbent materials; WO2013/007973, which describes non-negative pressure wound dressings; GB1618298.2 (filed on 28 Oct. 2016), GB1621057.7 (filed on 12 Dec. 2016), and GB1709987.0 (filed on 22 Jun. 2017), which describe multi-layered wound dressings; EP2498829 and EP1718257, which describe wound dressings; WO2006/110527, U.S. Pat. No. 6,759,566, and US2002/0099318, which describe compression bandages; U.S. Pat. Nos. 8,235,955 and 7,753,894, which describe wound closure devices; WO2013/175306, WO2016/174048, US2015/0190286, US2011/0282309, and US2016/0339158, which describe negative pressure wound therapy dressings, wound dressing components, wound treatment apparatuses, and methods. The disclosure of each of these applications is hereby incorporated by reference in its entirety.

Sensor Enabled Wound Monitoring or Therapy System

FIG. 1A illustrates a wound monitoring or therapy system 10. The system includes a sensor enabled wound dressing 22 connected to a control module 24. As is described herein, the dressing 22 can be placed on or in a wound of a patient and can utilize various sensors embedded or otherwise placed in the dressing 22 to collect measurement data from one or more of the wound or areas surrounding the wound, such as the periwound (which can include intact skin). The control module 24 can receive, store, and process data collected by the dressing 22. To facilitate communication, the dressing 22 can include one or more communication modules, such as one or more antennas as described herein. In some cases, the control module 24 can transmit one or more of commands and data to the dressing 22.

Wound dressing 22 can be disposable and control module 24 can be reusable. In some cases, wound dressing 22 can be reusable. In some cases, control module 24 can be a controller. In some cases, wound dressing 22 can be re-sterilized or otherwise sanitized or disinfected. In some cases, control module 24 can be disposable. In some cases, wound dressing 22 and control module 24 can be permanently connected and the combined wound dressing and control module be disposable, or reusable or re-sterilized or otherwise sanitized or disinfected. The control module 24 can be positioned on the wound dressing 22. The control module 24 can be spatially separated from the wound dressing 22, such as by a cable or another wired or wireless electrical connection. The control module 24 can include a power source (such as a battery), one or more processors, one or more data storage elements, and a communication device. In some cases, the control module 24 can include one or more sensors, such as a temperature sensor or light (or optical) sensors to gather information on patient or environmental conditions located away from the wound dressing 22. In some cases, the one or more sensors of the control module 24 can include an accelerometer, motion sensor or gyroscope.

The wound dressing 22 can include one or more indicators to communicate information to a user. The indicators can be visual, audible, haptic, or tactile. Communicated information can include measurement data, wound status, or the like.

The control module 24 can communicate data to a communication device 30 as requested, periodically, or the like. Communication can be performed over a wired or wireless interface, such as via near field communication (NFC), RFID, or the like when the communication device is placed in communication range. For example, communication range can be close proximity, such as within approximately 3 cm or less or more, to the control module 24. Communication device 30 can be placed in communication range by a clinician, such as during initialization and at the end of treatment. The control module 24 can respond with data to a command from the communication device 30 requesting data. Communication can be performed via transfer of hardware or data storage, such as one or more memory storage devices (for example, SD card). In some cases, communication can be performed non-electronically, such as visually, audibly, or tactilely, and one or more of the control module 24 or communication device 30 can provide an interface for such non-electronic communication of data.

The communication device 30 can be connected via a wired or wireless interface to a computing device 40, such as a personal computer, tablet, smartphone, or the like. For example, wired USB protocol can be used for communication of data between devices 30 and 40. As another example, communication of data can be performed via transfer of hardware or data storage, such as one or more memory storage devices (for example, SD card). In some cases, communication of data can be performed non-electronically, such as visually, audibly, or tactilely, and one or more of the communication device 30 or computing device 40 can provide an interface for such non-electronic communication of data.

Computing device 40 can further process data collected by the dressing 22. For example, the computing device 40 can aggregate data collected from the dressing 22 and perfusion determination device 70, which is configured to determine skin perfusion pressure and communicate data to the computing device 40 via a wired or wireless interface. For example, wired USB protocol can be used for communication between devices 70 and 40.

Computing device 40 can be configured to communicate via a wired or wireless interface with a remote computing device 50 that stores and processes medical data. In some cases, remote computing device 50 can be a cloud computing device, which includes one or more of remote storage, server, processing device, or any means of information storage. For example, remote computing device 50 can process and store medical data according with one or more applicable security and privacy standards, such as Health Insurance Portability & Accountability Act (HIPAA), European Union's Directive on Data Protection, or the like. Remote computing device 50 can make data provided by one or more of the computing device 40 or the mobile device 60 available for remote accessing and viewing, such as on a mobile device 60. In certain implementations, additional data can be added for storage on the remote computing device 50. For example, additional data can be added by the mobile device 60 via a dedicated app, web browser interface, or the like. The remote computing device 50 can process the data from one or more of the wound dressing 22, perfusion determination device 70, or the mobile device and assess or determine treatment plan, such as suggest or adjust one or more treatment therapies.

As described herein, mobile device 60 can take one or more images of a patient's wound. Such data can be transmitted via wired or wireless interface to the remote computing device 50. Although a smartphone is illustrated, mobile device 60 can be any suitable computing device that includes imaging functionality, such as a camera. Mobile device 60 can also collect additional data, such as data input by a healthcare provider in response to a questionnaire.

Sensor Enabled Substrates and Wound Dressings

A wound dressing that incorporates a number of electronic components, including one or more sensors, can be utilized in order to monitor characteristics of a wound. Collecting and analyzing data from a wound can provide useful insights towards determining whether a wound is on a healing trajectory, selecting proper therapy, determining whether the wound has healed, or the like.

Figure 1B:
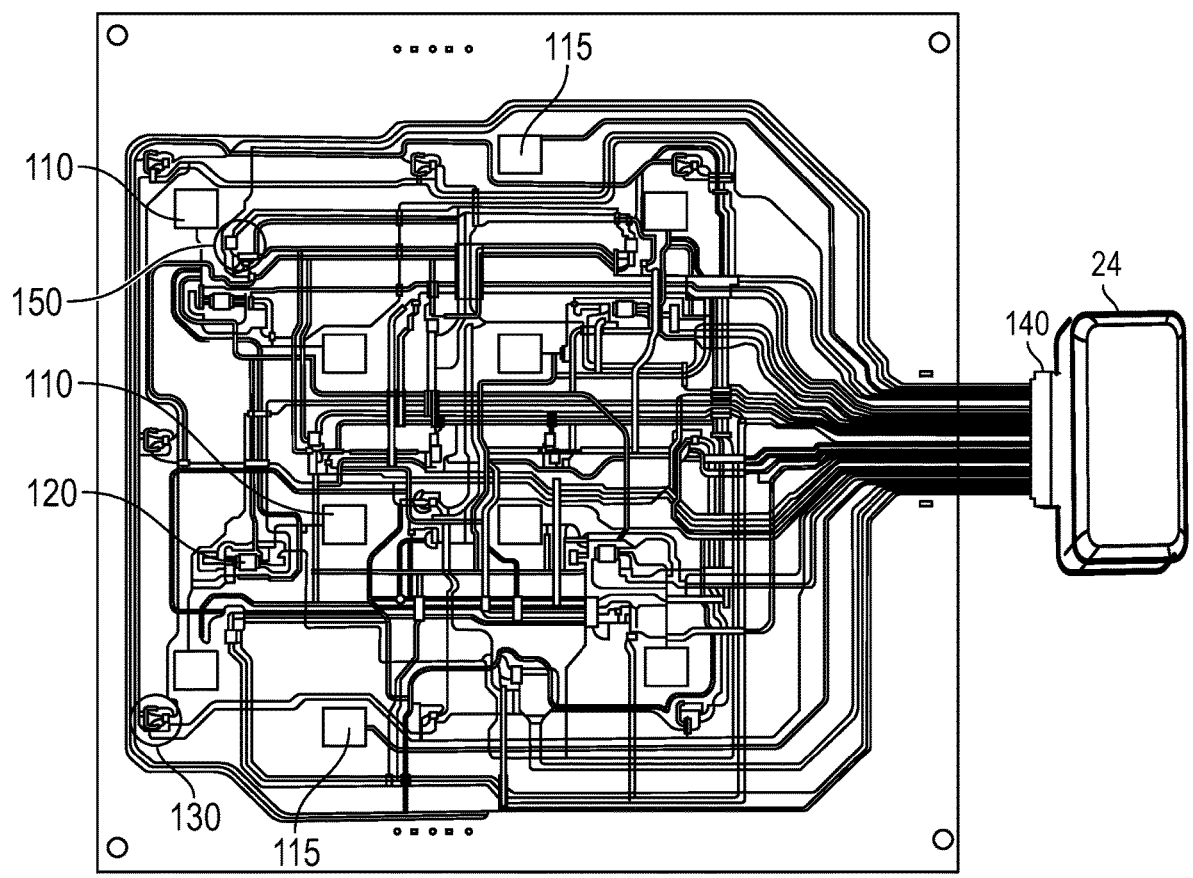
FIGS. 1B-1C illustrate substrates supporting electronic components.
Figure 1C:
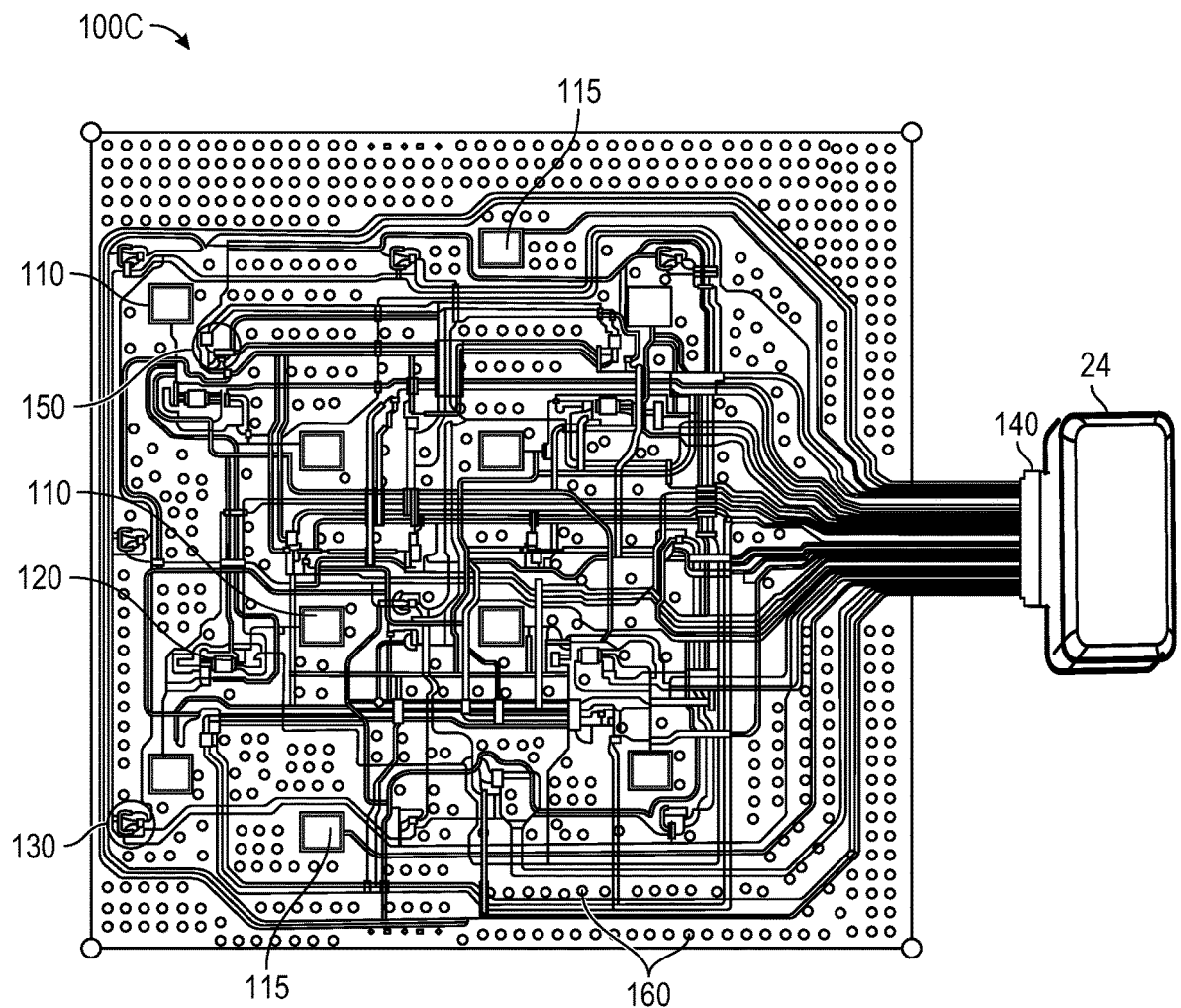

In some implementations, a number of sensor technologies can be used in wound dressings or one or more components forming part of an overall wound dressing apparatus. For example, as illustrated in FIGS. 1B-1C, one or more sensors can be incorporated onto or into a substrate (such substrate can be referred to as "sensor integrated substrate" or "sensor enable substrate"). The substrate is illustrated as having a square shape, but it will be appreciated that the substrate may have other shapes such as rectangular, circular, oval, etc. In some cases, a substrate supporting one or more sensors can be provided as an individual material layer that is placed directly or indirectly over or in a wound. The sensor integrated substrate can be part of a larger wound dressing apparatus. In some cases, the sensor integrated substrate is part of a single unit dressing. Additionally or alternatively, the sensor integrated substrate can be placed directly or indirectly over or in the wound and then covered by a secondary wound dressing, which can include one or more of gauze, foam or other wound packing material, a superabsorbent layer, a drape, a fully integrated dressing like the Pico or Allevyn Life dressing manufactured by Smith & Nephew, or the like.

The sensor integrated substrate can be placed in contact with a wound and can allow fluid to pass through the substrate while causing little to no damage to the tissue in the wound. The substrate can be flexible, elastic, extensible, or stretchable or substantially flexible, elastic, extensible, or stretchable in order to conform to or cover the wound. For example, the substrate can be made from a stretchable or substantially stretchable material, such as one or more of polyurethane, thermoplastic polyurethane (TPU), silicone, polycarbonate, polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material.

Stretchable or substantially stretchable material can be stretched to 5% or less or more, 10% or less or more, 20% or less or more, or more than 20% of its starting dimensions, such as length or width. In some cases, the stretchable or substantially stretchable material can return to within 5% or less or more of the starting dimensions (such as length or width) after being stretched.

In some cases, the substrate can include one or more flexible circuit boards, which can be formed of flexible polymers, including polyamide, polyimide (PI), polyester, polyethylene naphthalate (PEN), polyetherimide (PEI), along with various fluropolymers (FEP) and copolymers, or the like. One or more sensors can be incorporated into a two-layer flexible circuit. In some scenarios, the one or more circuit boards can be a multi-layer flexible circuit board.

In some cases, the sensor integrated substrate can incorporate adhesive, such as a wound contact layer as described herein, that adheres to wet or dry tissue. In some cases, one or more sensors, which can be positioned one or more flexible circuits, can be incorporated into any layer of the wound dressing. For example, a wound contact layer can have cutouts or slits that allow for one or more sensors to protrude out of the lower surface of the wound contact layer and contact the wound directly. In some situations, one or more sensors can be incorporated into or encapsulated within other components of a wound dressing, such as an absorbent layer.

As shown in FIGS. 1B, a sensor integrated substrate 100B can support a plurality of electronic components and a plurality of electrical connections interconnecting at least some of the components. The electronic components can be one or more of any electronic components described herein, such as a sensor, amplifier, capacitor, resistor, inductor, controller, processor, diode, or the like. The electrical connections can electrically connect one or more of the electronic components. The electrical connections can be traces or tracks printed on the substrate, such as using copper, conductive ink (such as ink that includes any one or any combination of silver, graphite, carbon, graphene, graphene oxide, carbon nanotube, nano-silver), nanotechnology-based conductive ink, organic conductive ink, etc.), or the like. At least some of the electrical connections can be flexible or stretchable or substantially flexible or stretchable.

The plurality of electronic components can include one or more impedance or conductivity sensors 110, which can be arranged in an outer 4×4 grid and an inner 4×4 grid as illustrated in FIGS. 1B-1C. Sensors 110 are illustrated as pads configured to measure impedance or conductivity of tissue across any pair of the pads. Two (or more) excitation pads 115 can be arranged as illustrated to provide the excitation signal across the pads, which is conducted by the tissue and responsive to which impedance or conductance of the tissue can be measured across the pads 110. Electronic components, such as one or more amplifiers 120, can be used to measure impedance or conductance of the tissue. Impedance or conductance measurements can be used to identify living and dead tissue, monitor progress of healing, or the like. The arrangement of the pads 110 in the inner and outer grids can be used to measure the impedance or conductance of the wound, perimeter of the wound, or tissue or areas surrounding the wound.

The plurality of electronic components can include one or more temperature sensors 130 configured to measure temperature of the wound or surrounding tissue. For example, nine temperature sensors arranged around the perimeter of the substrate 100B. One or more temperature sensors can include one or more thermocouples or thermistors. One or more temperature sensors can be calibrated and the data obtained from the one or more sensors can be processed to provide information about the wound environment. In some cases, an ambient sensor measuring ambient air temperature can also be used to assist in eliminating problems associated with environment temperature shifts.

The plurality of electronic components can include one or more optical sensors 150. One or more optical sensors 150 can be configured to measure wound appearance or image the wound. In some cases, a light source or illumination source that emits light and a light sensor or detector that detects light reflected by the wound are used as one or more optical sensors. The light source can be a light emitting diode (LED), such as one or more of white LED, red, green, blue (RGB) LED, ultraviolet (UV) LED, or the like. The light sensor can be one or more of an RGB sensor configured to detect color, infrared (IR) color sensor, UV sensor, or the like. In some cases, both the light source and detector would be pressed up against the skin, such that light would penetrate into the tissue and take on the spectral features of the tissue itself. In some scenarios, one or more optical sensor can include an imaging device, such as a charge-coupled device (CCD), CMOS image sensor, or the like.

In some cases, ultra bright LEDs, an RGB sensor, and polyester optical filters can be used as components of the one or more optical sensors to measure through tissue color differentiation. For example, because surface color can be measured from reflected light, a color can be measured from light which has passed through the tissue first for a given geometry. This can include color sensing from diffuse scattered light, from an LED in contact with the skin, or the like. In some cases, an LED can be used with a proximal RGB sensor to detect the light which has diffused through the tissue. The optical sensors can image with diffuse internal light or surface reflected light.

One or more of the plurality of electronic components can be controlled by a control module. The control module can receive and process one or more measurements obtained by the one or more sensors. An external control module, such as 24 illustrated in FIG. 1A, can be connected to at least some of the plurality of electronic components via a connector (for example, connector 140 in FIGS. 1B-1C). In some cases, the connector 140 can be positioned at the end of a conductive track portion as illustrated in FIG. 1C or attached to the conductive track portion at a position away from the end as illustrated in FIG. 1B (such as, attached to the top of the track portion with glue). The control module can include one or more controllers or microprocessors, memory, or the like. In some cases, one or more controllers can be positioned on the substrate, and the connector 140 is not used. In some cases, data and commands can be communicated wirelessly, such as by a transceiver positioned on the substrate, and the connector 140 is not used.

In some cases, additional or alternative sensors can be positioned on the substrate, such as one or more pH sensors, pressure sensors, perfusion sensors, or the like.

In some cases, a substrate can be perforated as illustrated in FIG. 1C. A plurality of perforations 160 can be formed in the substrate 100C, allowing fluid to pass through the substrate. It may be advantageous to use a perforated substrate in conjunction with application of negative pressure wound therapy, during which reduced pressure is applied to the wound covered by a dressing and which causes removal of fluid (such as wound exudate) from the wound. Perforations 160 can be formed around a plurality of electronic components and connections as illustrated in FIGS. 1B-1C. Perforations 160 can be formed as slits or holes. In some cases, perforations 160 can be small enough to help prevent tissue ingrowth while allowing fluid to pass through the substrate.

In some cases, the substrate can be coated to encapsulate or coat one or more of the substrate or components supported by the substrate. Coating can provide biocompatibility, shield or protect the electronics from coming into contact with fluids, provide padding for the electronic components to increase patient comfort, or the like. Such coating can be sometimes referred to as "conformal coat" or "soft coat." Soft coat can be stretchable or substantially stretchable. Soft coat can be hydrophobic or substantially hydrophobic.

Soft coat can be formed from one or more suitable polymers, adhesives, such as 1072-M adhesive (for example, Dymax 1072-M), 1165-M adhesive (such as, Dymax 1165-M), parylene (such as, Parylene C), silicones, epoxies, urethanes, acrylated urethanes, acrylated urethane alternatives (such as, Henkel Loctite 3381), or other suitable biocompatible and substantially stretchable materials. Soft coat can be thin coating, for example, from about 80 microns or less up to several millimeters or more. Soft coat can have hardness lower than about A100, A80, A50 or lower. Soft coat can have elongation at break higher than about 100%, 200%, 300% or more. Soft coat can have viscosity of about 8,000-14,500 centipoise (cP). In some cases, coating can have viscosity no less than about 3,000 cP. In some cases, coating can have viscosity less than about 3,000 cP.

In some cases, while it may be desirable for a substrate to be stretchable or substantially stretchable to better conform to or cover the wound, at least some of the electronic components or connections may not be stretchable or flexible. In such instances, undesirable or excessive localized strain or stress may be exerted on the one or more electronic components, such as on the supporting area or mountings of an electronic component, when the substrate is positioned in or over the wound. For example, such stress can be due to patient movement, changes in the shape or size of the wound (such as, due to its healing), or the like. Such stress may cause movement, dislodgment, or malfunction of the one or more electronic components or connections (for example, creation of an open circuit from a pin or another connector becoming disconnected). Alternatively or additionally, it may be desirable to maintain the position of one or more electronic components, such as one or more sensors, in the same or substantially same location or region with respect to the wound (such as, in contact with the wound) so that measurements collected by the one or more electronic components accurately capture changes over time in the same or substantially same location or region of the wound. While the surface of the stretchable substrate may move when, for example, the patient moves, it may be desirable to maintain same or substantially same locations of one or more electronic components relative to the wound.

To address these problems, in some cases, non-stretchable or substantially non-stretchable coating (such coating can sometimes be referred to as "hard coat") can be applied to one or more electronic components, one or more electrical connections, or the like. Hard coat can provide one or more of reinforcement or stress relief for one or more electronic components, one or more electrical connections, or the like. Hard coating can be formed from acrylated or modified urethane material. For example, hard coat can be one or more of Dymax 1901-M, Dymax 9001-E, Dymax 20351, Dymax 20558, Henkel Loctite 3211, or another suitable material. Hard coat can have viscosity from about 13,500 cP to 50,000 cP before being cured or from about 3,600 cP to about 6,600 cP before being cured. In some cases, hard coat can have viscosity of no more than about 50,000 cP. Hard coat can have hardness from about D40 to about D65 and/or linear shrinkage of about 1.5-2.5%.

Any of the hard or soft coats described herein can be applied by one or more of laminating, adhering, welding (for instance, ultrasonic welding), curing by one or more of light, UV, thermal (such as, heat), or the like. Any of the hard or soft coat described herein can be transparent or substantially transparent to facilitate transmission of light through the coating, such as for optical sensing. Any of the coatings described herein can retain bond strength when subjected to sterilization, such as EtO sterilization. Any of the coatings described herein can be modified to fluoresce, such as under UV light.

In some implementations, borders or edges of the substrate can be smoothed by cuts, have smooth contours, include fibers, or the like to improve patient comfort.

In some cases, the substrate can include one or more antennas for wireless communication. For example, one or more antennas can be printed as one or more connections or traces on the substrate. The one or more antennas can be used to communicate measurement data collected by the one or more sensors without using a controller, such as the control module 24. The one or more antennas can additionally be used to receive power wirelessly from a power source. In certain cases, the one or more antenna traces can be positioned on a substantially non-stretchable material (as described herein) such that the resonant frequencies of the one or more antennas remain fixed when the substrate is placed under stress when in use on a patient. Fixing the one or more resonant frequencies can be advantageous for certain communication protocols, such as RFID.

Any of the systems and methods disclosed herein can be used in combination with any of the features disclosed in one or more of G.B. Application No. 1905696.9, entitled "Sensor Integrated Dressings And Systems," filed Apr. 24, 2019, which describes various dressings and components thereof; and G.B. Application No. 1905696.9, entitled "Sensor Integrated Dressings And Systems," filed Jan. 20, 2019, which describes various dressings and components thereof. The disclosure of each of these applications is hereby incorporated by reference in its entirety.

Electrical Connections on Substrate

Figure 2A:
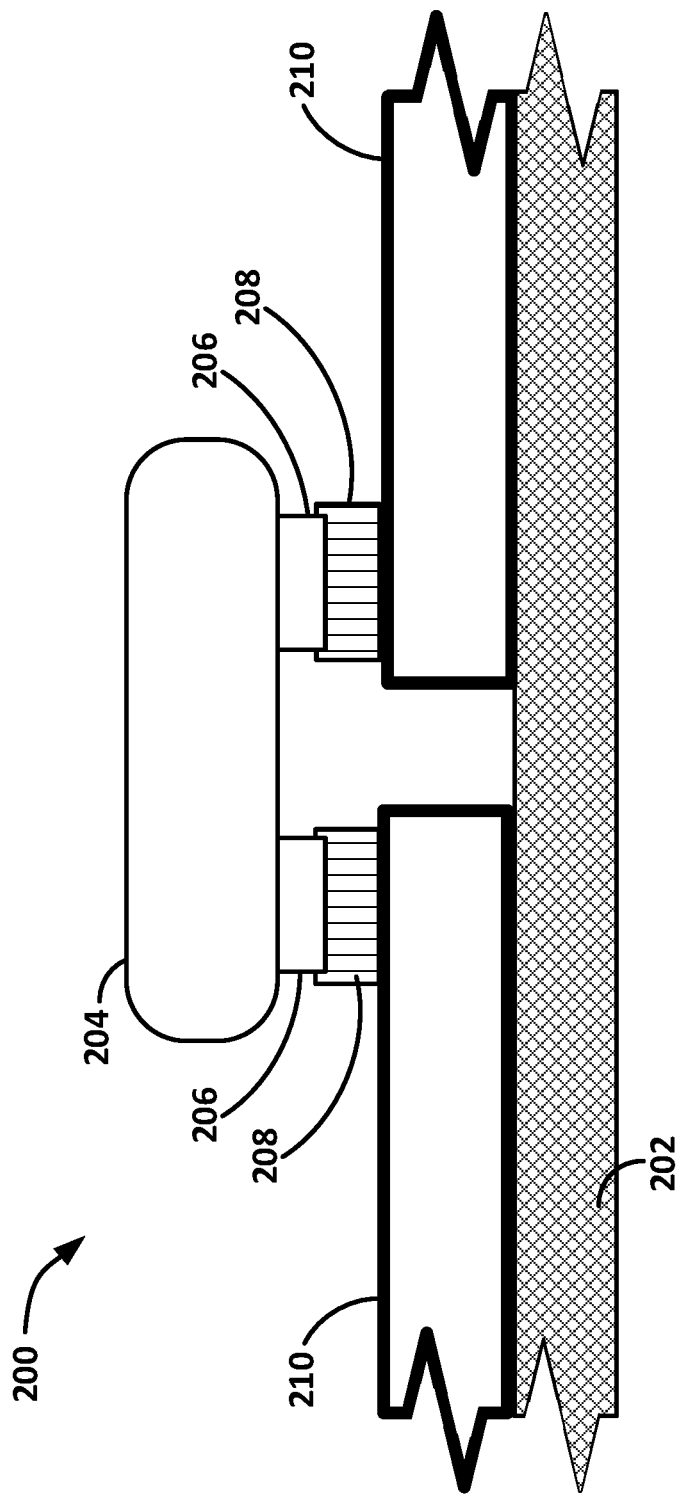
FIG. 2A illustrates a cross-sectional view of a portion of an example wound monitoring and/or therapy apparatus that includes an electronic component 204 electrically coupled to a substrate via soldering paste and a plurality of electrical connections.

FIG. 2A illustrates a cross-sectional view of a portion of an example wound monitoring and/or therapy apparatus 200 that includes an electronic component 204 electrically coupled to a substrate 202 via soldering paste 208 and a plurality of electrical connections 210. It will be appreciated that the wound monitoring and/or therapy apparatus 200 can include fewer or more components as desired. For example, the substrate 202 can be electrically coupled to one or more different or additional electronic components via the same or other electrical connections. Furthermore, in some cases, the electronic component 204 can be coupled directly to the electrical connections 210, for example rather than being indirectly coupled to the electrical connections 210 via the soldering paste 208.

The electronic component 204 can be the same or similar to any electronic component described herein, such as a sensor, amplifier, capacitor, resistor, inductor, controller, processor, diode, connector, or the like. As illustrated, the electronic component 204 can include a plurality of electrical connectors 206. For example, the electronic component 204 can include one or more electrical connectors 206 for power, ground, inputs, outputs, data, etc. In some cases, the electrical connectors 206 include one or more of electrical pads, pins, or tabs. The electrical connectors 206 can be utilized to electrically connect the electronic component 204 to one or more other electronic components, or one or more electrical connections 210, such as traces or tracks printed on the substrate 202.

The substrate 202 can be the same or similar to any combination of one or more of the substrates described herein. For example, the substrate 202 can include any combination of one or more features or characteristics of the sensor integrated substrate 100B of FIG. 1B or the sensor integrated substrate 100C of FIG. 1C. For example, in some cases, the substrate 202 is flexible, elastic, extensible, or stretchable or substantially flexible, elastic, extensible, or stretchable in order to conform to or cover the wound. In some cases, it can be advantageous to utilize electrical connections 210 that can be stretched. In some cases, areas of the substrate 202 that include electronic components 204 can be more rigid, or less flexible, than other areas of the substrate 202. In some cases, the substrate 202 can include one or more fibers, such as cotton or other textile fibers.

The electrical connections 210 can be printed on or integrated with the substrate 202. For example, the electrical connections 210 can be screen printed on to the substrate. In some cases, the electrical connections 210 allow various electrical signals, connections, and/or power to be routed on, off, around, or through the substrate 202. For example, a combination of one or more of the electrical connections 210 can electrically connect various points of the substrate and/or electrically connect various electronic components positioned on or off the substrate 202.

In some cases, one or more of the electrical connections 210 include traces or tracks printed on the substrate 202. For example, the electrical connections 210 can include a combination of one or more of copper, conductive inks (for example, inks that include one or more of silver, graphite, carbon, graphene, graphene oxide, carbon nanotube, nanosilver), nanotechnology-based conductive inks, organic conductive inks, etc., conductive glues, conductive tapes, fibers, soldering pastes, or the like. As described herein, in some cases, the electrical connections 210 can include one or more types of conductive inks, conductive glues, conductive tapes, fibers, soldering pastes, or the like. For example, a first type of conductive ink may be utilized in a first location on the substrate 202, and a second type of conductive ink may be utilized in a second location on the substrate 202. In some such examples, the use or placement of different types of conductive inks can be based at least in part on one or more characteristics or properties of the conductive inks. For instance, a more conductive ink may be utilized in regions or areas for soldering, and a different ink (for example, one whose resistance doesn't drastically change when the ink is stretched) can be utilized in one or more other areas on the substrate 202. In this way, the wound monitoring and/or therapy apparatus 200 can make use of the advantages of multiple conductive inks. As another example, a more conductive ink, or an ink having a smaller impedance, may be utilized for communication signals, such as antenna traces.

In some cases, one or more of portions of soldering paste 208 can be printed on the electrical connections 210 or the substrate 202. For example, the soldering paste 208 can be printed on the electrical connections 210 and/or the substrate 202, and then it can be heated (along with the rest of the board) to melt the soldering paste 208 and form a mechanical bond as well as an electrical connection. In some cases, the soldering paste 208 is replaced with a different material, such as a conductive glue or conductive tape. In some cases, the wound monitoring and/or therapy apparatus 200 does not include soldering paste 208. For example, in some cases, the electronic component 204 can be coupled directly to the electrical connections 210 rather than being indirectly coupled to the electrical connections 210 via the soldering paste 208.

Multiple Conductive Inks

Different types of conductive inks can have different properties and/or characteristics. For example, the impedance, impedance variance (for example, due to stretching of the ink), thermal conductivity, electrical conductivity, etc. can vary based on the type of ink used. It follows that some inks may be better for some purposes, while other inks may be better for other purposes. Accordingly, in some cases, a wound monitoring and/or therapy apparatus 200 can utilize electrical connections 210 that include multiple types of conductive inks. Furthermore, in some cases, a particular type of conductive ink can be arranged on the substrate 202 based on its advantageous properties. In this way, in some implementations, two or more different types of conductive inks can be arranged on (or coupled to) the substrate 202, for example, to exploit the beneficial characteristics of the different types of conductive inks. However, it will be understood that, in some cases, one or more types of conductive ink can be arranged on the substrate 202 without regard to, or in opposition to, one or more of its characteristics (e.g., thermal conductivity, electrical conductivity, impedance, flexibility, etc.)

Figure 2B:
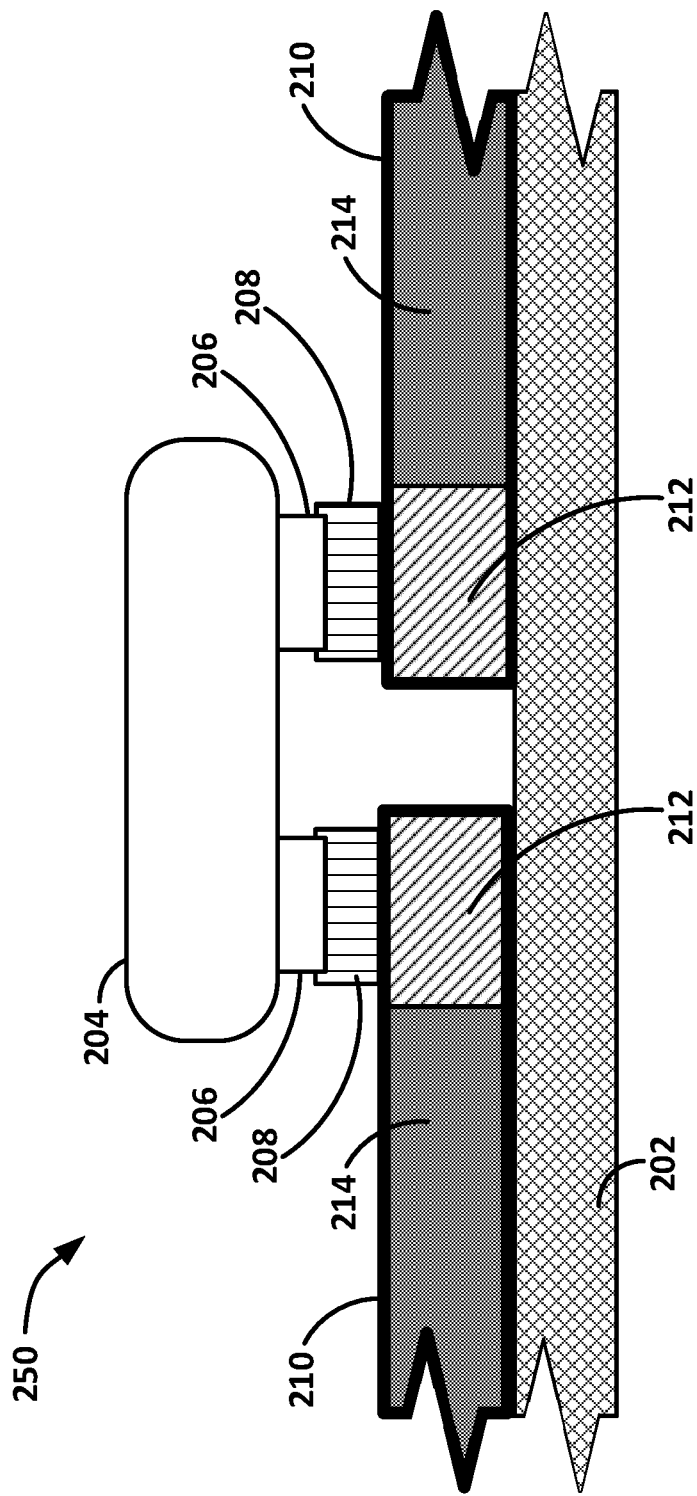
FIG. 2B illustrates the cross-sectional view of FIG. 2A and further illustrates an example of the electrical connections including multiple types of conductive ink.

Similar to FIG. 2A, FIG. 2B illustrates a cross-sectional view of a portion of an example wound monitoring and/or therapy apparatus 250 that includes an electronic component 204 electrically coupled to a substrate 202 via soldering paste 208 and a plurality of electrical connections 210. FIG. 2B further illustrates an example of the electrical connections 210 including multiple types of conductive ink. Specifically, the electrical connections 210 include a first type of conductive ink 212 (sometimes referred to herein as a first ink 212) and a second type of conductive ink 214 (sometimes referred to herein as a second ink 214). It will be appreciated that although FIG. 2B is discussed with respect to conductive ink, the electrical connections 210 can additionally or alternatively include one or more metals, conductive glues, conductive tapes, fibers, florescent elements, or the like. Furthermore, it will be appreciated that although only two types of conductive inks are shown, additional or different types of conductive inks can be utilized.

In some cases, the first ink 212 and the second ink 214 have one or more different characteristics, such as different thermal conductivity, electrical conductivity, impedance, flexibility, or the like. For example, in some cases, the first ink 212 and the second ink 214 have different electrical conductivities. For instance, an ink with a relatively high conductivity may allow for thinner traces and/or may allow for improved electrical connections. As such, in some cases, the ink 212 or 214 having the higher conductivity can be utilized in areas for various connections, such as contact areas of the electronic components 204 (for example, the areas to which the electronic components 204 connect to the substrate) and/or ink footprints around the electronic components 204. Furthermore, in some cases, the ink 212 or 214 having the higher conductivity can be utilized for mounting electronic components 204 to the substrate 202. Furthermore, in some cases, the ink 212 or 214 having the higher conductivity can be utilized for communication signals, such as antenna traces. As shown in the example of FIG. 2B, the first ink 212 is utilized to mount the electronic component 204. Thus, in some cases, the first ink 212 is more conductive than the second ink 214. However, in some cases, the second ink 214 is more conductive than the first ink 212, or the first ink 212 and the second ink 214 have approximately equal conductivities. In some cases, one ink is more conductive than the other ink at least because it includes more or a particular metal (e.g., silver), it has a greater thickness, or a greater width.

In some cases, the first ink 212 and the second ink 214 have different thermal conductivities. For example, in some cases, the first ink 212 has a higher thermal conductivity than does the second ink 214, while in other cases, the second ink 214 has a higher thermal conductivity than the does the first ink 214.

In some cases, the first ink 212 and the second ink 214 attach, adhere, or bond differently to soldering paste 208. For example, in some cases, the first ink 212 makes a good electrical connections with the soldering paste 208, and the second ink 212 does not make as good of an electrical connection with the soldering paste 208 as does the first ink 212. In some cases, the soldering paste 208 at least partially overlaps with one or more of the first ink 212 or the second ink 214. For example, the soldering paste 208 can be one layer of multiple layers on the substrate 202.

In some cases, the first ink 212 and the second ink 214 have different impedance variabilities. For example, when stretched, the impedance on an ink may change. For instance, in some cases, a conductive ink 212 or 214 may have a relatively low impedance variability such that, when stretched, the impedance of the ink remains relatively constant. As another example, in some cases, a conductive ink 212 or 214 may have a relatively high impedance variability such that, when stretched, the impedance of the ink fluctuates. In some cases, the first ink 212 has a higher impedance variability than does the second ink 214, while in other cases, the second ink 214 has a higher impedance variability than the does the first ink 214. As described herein, the substrate 202 is substantially flexible and is prone to flexing. As such, in some cases, to minimize or limit impedance changes due to stretching, it can be advantageous to utilize the ink with a lower impedance variability in at least some of the areas on the substrate 202 that are prone to flex or stretch.

As shown, in the example of FIG. 2B, the second ink 214 is utilized for making electrical connections other than those for mounting the electronic components 204. For example, the second ink 214 can form conductive traces that electrically connect various points or electronic devices on the substrate 202. As another example, the second ink 214 can electrically couple two different portions of first ink 212 or create a connection to a component or device that resides off of the substrate 202.

It will be appreciated that the arrangement of the first ink 212 and the second ink 214 can change, as desired, or can change, for example based on the properties and/or characteristics of the first and second inks 212, 214. For example, in some cases, the first ink 212 and the second ink 214 are at least partially mixed or are at least partially overlapping. As another example, the first and second inks 212, 214 can be shorter, longer, thinner, or thicker than illustrated. Furthermore, in some cases, at least some portions of the first ink 212 and the second ink 214 are directly connected to each other. In some cases, at least some portions of the first ink 212 and the second ink 214 are indirectly connected to each other. For example, at least some portions of the first ink 212 and the second ink 214 can be connected to each other via conductive glue, conductive tape, or the like.

Furthermore, in some cases, the electrical connections 210 can include a fewer or greater number of types of conductive ink. For instance, a particular electrical connection 212 can include a first conductive ink, while a different electrical connection 212 can include a second conductive ink and a third conductive ink.

Figure 2C:
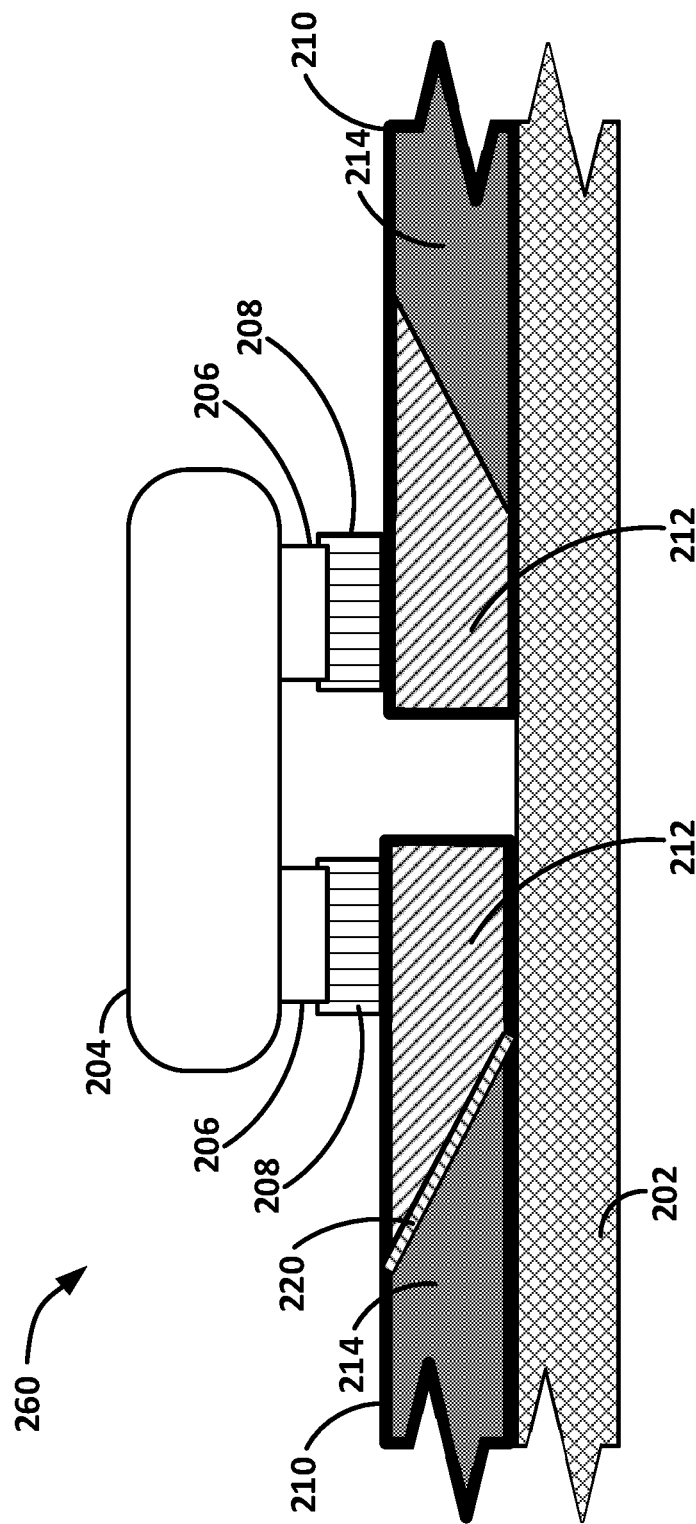
FIG. 2C illustrates the cross-sectional view of FIG. 2A and further illustrates an example of the overlapping electrical connections.

Similar to FIGS. 2A and 2B, FIG. 2C illustrates a cross-sectional view of a portion of an example wound monitoring and/or therapy apparatus 260 that includes an electronic component 204 electrically coupled to a substrate 202 via soldering paste 208 and a plurality of electrical connections 210. FIG. 2C further illustrates an example of the electrical connections 210 including multiple types of conductive ink (e.g., first ink 212 and second ink 214) and a conductive medium 220 between the multiple types of conductive ink.

In some cases, the first ink 212 and the second ink 214 can at least partially overlap. For example, the first ink 212 and the second ink 214 can at least partially overlap at joining points or the points at which the first ink 212 and the second ink 214 converge. In some cases, overlapping the inks 212 and 214 at the convergence point can improve an electrical connection between the first ink 212 and the second ink 214, for example, as compared to connecting them in a side-by-side manner. Although illustrated as the first ink 212 extending over so as to cover partly at least a portion of the second ink 214, in some cases, to overlap the inks, at least one portion of the second ink 214 extends over so as to cover partly at least a portion of the first ink 212. Furthermore, it will be understood that the first ink 212 and the second ink 214 can have various configurations. For example, in some cases, at least some portions of the first ink 212 and the second ink 214 are side-by-side. As another example, in some cases, at least some portions of the first ink 212 and the second ink 214 are mixed together or are layered on each other.

In some cases, the first ink 212 and the second ink 214 can be connected together using a conductive medium 220. For example, the conductive medium 220 can include soldering paste, conductive glue, conductive tape, or the like. In some cases, the conductive medium 220 improves the connectivity between the first ink 212 and the second ink 214. However, it will be understood that, in some cases, the first ink 212 and the second ink 214 are directly connected, without a conductive medium 220 in between. In some cases, any of the wound monitoring and/or therapy apparatuses 200, 250, 260 or 270 can include an isolation mask or layer. For example, an isolation mask can be printed between two or more electrical connections 210 in order keep the electrical connections 210 isolation. In some cases, the isolation mask allows stacking or layering of electrical connections 210 or electronic component 204, such that the isolation mask electrically separates the stacked electrical connections 210 or electronic components 204.

Fibers

Figure 2D:
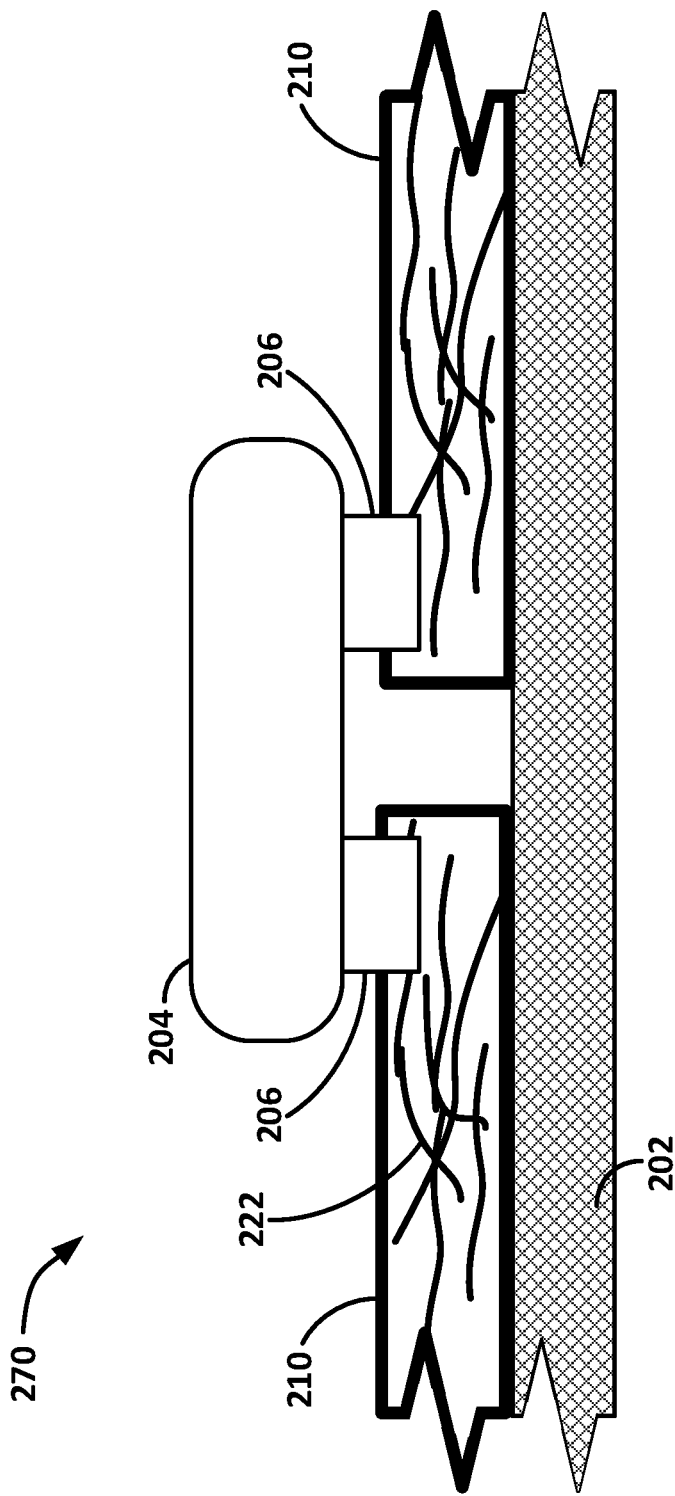
FIG. 2D illustrates the cross-sectional view of FIG. 2A and further illustrates an example of the electrical connections including one or more fibers.

Similar to FIGS. 2A-2C, FIG. 2D illustrates a cross-sectional view of a portion of an example wound monitoring and/or therapy apparatus 270 that includes an electronic component 204 electrically coupled to a substrate 202 via a plurality of electrical connections 210. FIG. 2D further illustrates an example of the electrical connections 210 including a plurality of electrical textiles 222 embedded in at least a portion (e.g., in the conductive ink, conductive medium, etc.) of the electrical connections 210. In some cases, the electrical textiles 222 can lower impedance variability due to stretching of the electrical connection 210. For example, in some cases, during stretching of the electrical connection 210, the electrical textiles 222 can move around within the electrical connection 210, but can maintain a connection with other electrical textiles 222 in the electrical connection 210. In this way, the electrical textiles 222 can prevent or limit changes in impedance due to stretching.

As illustrated, one or more of the electrical connections 210 can include the electrical textiles 222. For instance, in cases in which the electrical connections 210 include conductive ink, one or more electrical textiles 222 can be in the conductive ink. In some cases, electrical textiles 222 can be utilized in conductive inks that are prone to impedance variability due to stretching, such as in some examples of the first ink 212. In some cases, utilizing electrical textiles 222 in this way allow the electrical connections 210 to be thinner, or include thinner traces.

In some cases, the electrical textiles 222 can include a fiber, such as a single type of fiber or a blend of two or more types of fibers. For example, the electrical textiles 222 can include, but are not limited to, cotton, wool, jute, silk, polyester, polypropylene, nylon, Kevlar, or synthetic fibers.

It will be appreciated that the electrical textiles 222 can be embedded in different patterns and densities, and that the electrical textiles 222 can have one or more different lengths. For example, in some cases, the electrical textiles 222 include one or more continuous strands of fiber 222 that extend throughout the length of an electrical connection 210. As another example, in some cases, the electrical textiles 222 include a plurality of relatively short electrical textiles 222. For instance, during stretching of the electrical connection 210, one or more electrical textiles 222 can move within the electrical connection 210 to move toward or away from other electrical textiles 222. In some cases, at least some of the electrical textiles 222 remain in contact with each other. For example, the electrical textiles 222 can be tightly condensed into the electrical connection 210. In some cases, at least some of the electrical textiles 222 do not touch any other electrical textiles 222. For example, the electrical textiles 222 can be spaced throughout the electrical connection 210.

As illustrated, in some cases, the electrical connection 210 is directly coupled to the electrical connectors 206. However, it will be understood that the electrical connection 210 can be indirectly coupled to the electrical connectors 206, for example via soldering paste or conductive glue.

Quality Control

In some cases, the electrical connections 210 can include one or more components or markers, which can allow for quality control of one or more various connections. For example, in some cases, the electrical connections 210 include a fluorescent component. In some cases, a fluorescent component can be used for quality control, for example, checking the connections under UV light. As another example, in some cases, the electrical connections 210 can include radio transparent material that can be visible, or seen under x-ray or MM. In some cases, these components or markers can be biodegradable. In some cases, these markers could be used for quality control and/or can allow a user to check whether electronics are present in the wound and/or wound dressing, or where the electronics are present.

Conductive Inks

Figure 3B:
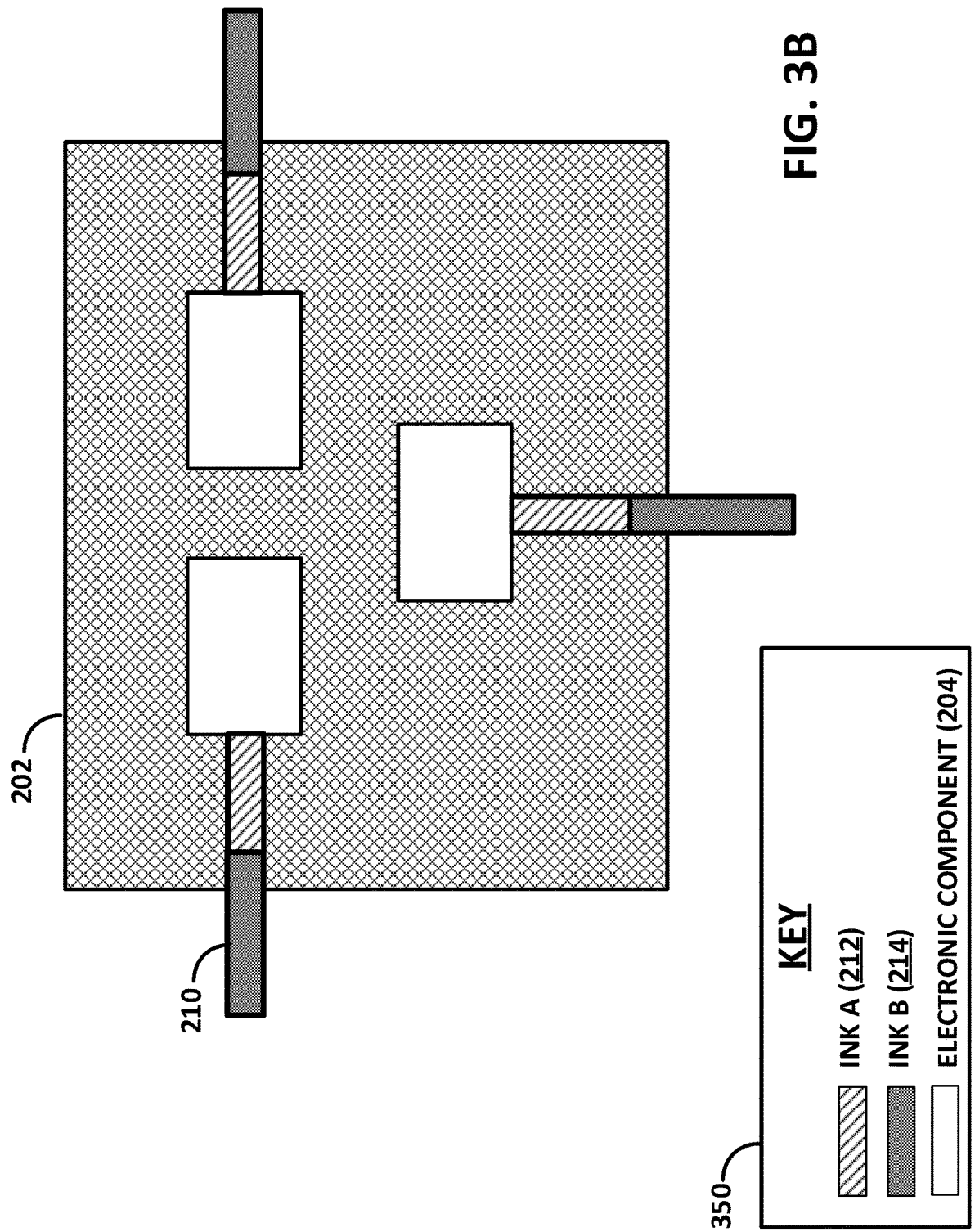
Figure 3C:
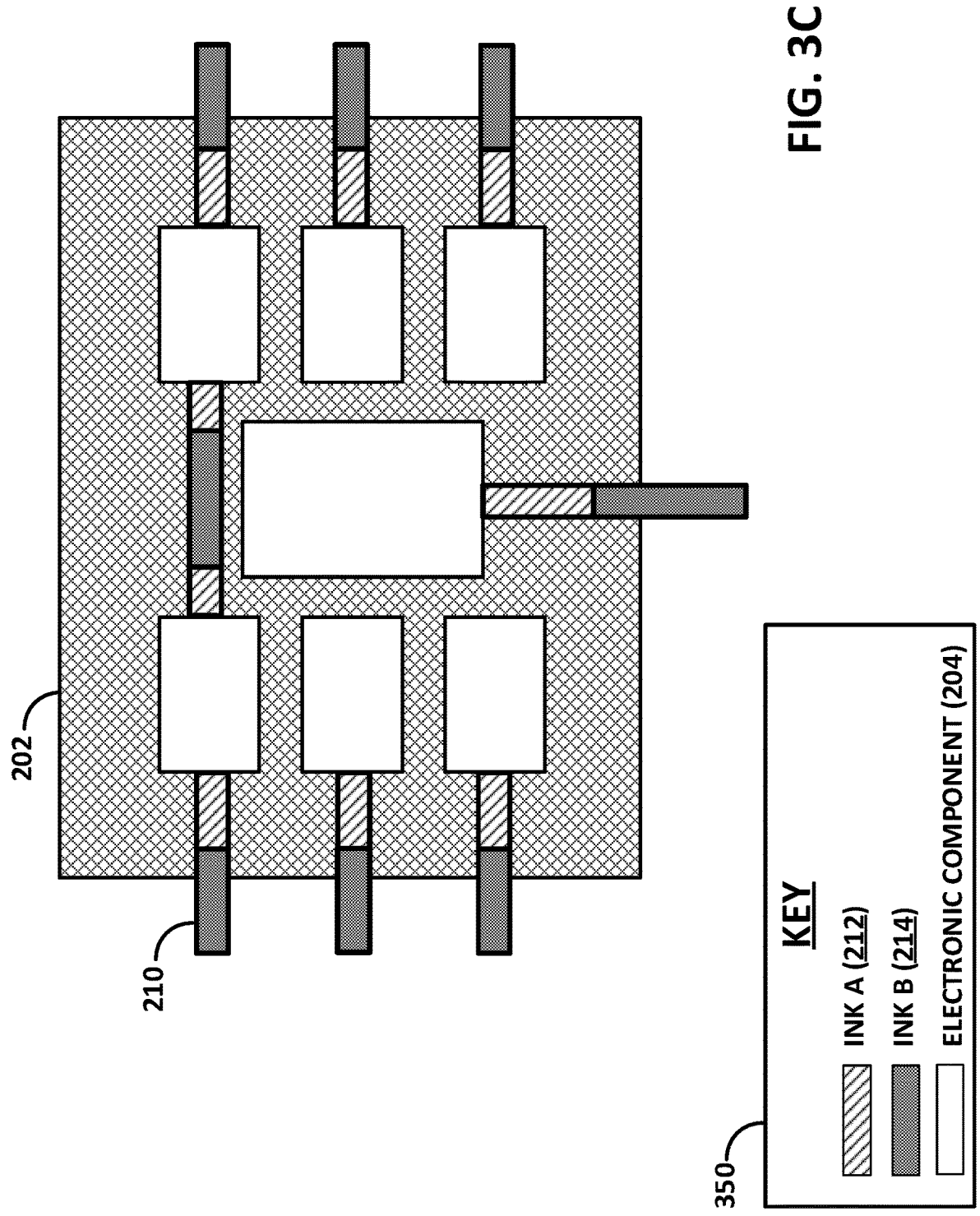

FIGS. 3A-3C illustrate substrates 202 that support a plurality of electronic components 204 and a plurality of electrical connections 210 electrically connecting one or more of the electronic components 204. As discussed herein, the electrical connections 210 can include a first type of conductive ink 212 of a second type of conductive ink 214. Furthermore, as described herein, the first ink 212 and the second ink 214 can have one or more different characteristics or properties, such as different impedance, impedance variance (for example, due stretching of the ink), thermal conductivity, electrical conductivity, or the like.

As described herein, in some cases, the substrate 202 is flexible, elastic, extensible, or stretchable or substantially flexible, elastic, extensible, or stretchable in order to conform to or cover the wound. Thus, in some cases, it can be advantageous to utilize electrical connections 210 that can be stretched. Furthermore, it can be advantageous to utilize electrical connections 210 whose properties (for example, resistance) are not substantially affected when the electrical connection 210 is stretched. In some cases, the second ink 214 may have less resistance variability due to stretching than does the first ink 212. In some such examples, the second ink 214 may be selected to form portions of the electrical connections 210 that reside on areas of the substrate 202 that are likely to be flexed. For example, as illustrated in FIGS. 3A-3C, the electrical connections 210 that extend across the substrate 202 can include the second ink 214.

In some cases, areas of the substrate 202 that include electronic components 204 can be more rigid, or less flexible, than other areas of the substrate 202. In some such cases, the electrical connection 210 proximate (for example, under and/or around) the electronic component 204 can include the first ink 212. For example, as illustrated in FIGS. 3A-3C, portions of the electrical connections 210 that are proximate an electronic component 204 can include the first ink 212, while other portions of the electrical connections 210 can include the second ink 214. In this way, the second ink 214 can be utilized to allow for electrical connections across the substrate 202 while also minimizing impedance changes due to stretching, and the first ink 212 can be utilized for its enhanced electrical and thermal conductivity, as compared to the second ink 214.

Other Variations

In some cases, one or more electronic components can be positioned on the side of a substrate opposite the side that faces the wound. Systems and methods described herein are equally applicable to such substrates. Although certain embodiments described herein relate to wound dressings, systems and methods disclosed herein are not limited to wound dressings or medical applications. Systems and methods disclosed herein are generally applicable to electronic devices in general, such as electronic devices that can be worn by or applied to a user.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A sensor sheet of a wound monitoring and/or therapy apparatus, the sensor sheet comprising:
   a plurality of electronic components comprising a first electronic component having a first electrical connector configured to electrically connect the first electronic component;
   a substantially flexible substrate having a first, wound-facing side supporting the plurality of electronic components and a second side opposite the first side:
   a track of first conductive ink residing on the substantially flexible substrate, the first conductive ink with a first impedance, and wherein the track of the first conductive ink is electrically coupled to the first electrical connector of the first electronic component; and
   a track of second conductive ink residing on the substantially flexible substrate, the second conductive ink with a second impedance different from the first impedance, and wherein the track of the second conductive ink is electrically coupled to the track of first conductive ink.

2. The sensor sheet of claim 1, further comprising a soldering paste electrically coupled between the first electrical connector and the first electronic component, wherein the soldering paste electrically couples the first electrical connector and the first electronic component.

3. The sensor sheet of claim 1, wherein the track of the second conductive ink is electrically coupled to the first electronic component via the track of the first conductive ink.

4. The sensor sheet of claim 1, wherein the track of the first conductive ink is a first track of the first conductive ink, wherein the sensor sheet further comprises a second track of the first conductive ink coupled to the track of the second conductive ink, and wherein the second track of the first conductive ink is electrically coupled to the first track of the first conductive ink via the track of the second conductive ink.

5. The sensor sheet of claim 1, wherein the track of the first conductive ink is a first track of the first conductive ink, wherein the plurality of electronic components further comprises a second electronic component having a second electrical connector, wherein the sensor sheet further comprises a second track of the first conductive ink coupled to the second electrical connector of the second electronic component.

6. The sensor sheet of claim 5, wherein the track of the second conductive ink is further coupled to the second track of the first conductive ink.

7. The sensor sheet of claim 5, wherein the first electronic component is electrically coupled to the second electronic component via the first track of the first conductive ink, the track of the second conductive ink, and the second track of the first conductive ink.

8. The sensor sheet of claim 5, wherein the track of the second conductive ink is a first track of the second conductive ink, wherein the sensor sheet further comprises a second track of the second conductive ink coupled to the second track of the first conductive ink.

9. The sensor sheet of claim 1, wherein the first electronic component comprises at least one of a sensor, an amplifier, a capacitor, a resistor, an inductor, a controller, a processor, a diode, or a connector.

10. The sensor sheet of claim 1, wherein at least one of the first conductive ink or the second conductive ink comprises silver ink.

11. The sensor sheet of claim 1, wherein an impedance variance due to stretching of the second conductive ink is smaller than an impedance variance due to stretching of the first conductive ink.

12. The sensor sheet of claim 1, wherein the first conductive ink has a first width, wherein the second conductive ink has a second width that is larger than the first width.

13. The sensor sheet of claim 1, wherein a thermal conductivity of the first conductive ink is higher than a thermal conductivity of the second conductive ink.

14. The sensor sheet of claim 1, wherein at least one of the first conductive ink or the second conductive ink comprises an electrical textile, and wherein the electrical textile comprises cotton.

15. The sensor sheet of claim 1, wherein the first conductive ink comprises a fiber, and wherein the fiber reduces an impedance variance due to stretching of the first conductive ink.

16. The sensor sheet of claim 1, wherein the first impedance is greater than the second impedance.

17. The sensor sheet of claim 1, wherein the first conductive ink is more conductive than the second conductive ink.

18. The sensor sheet of claim 1, wherein at least a portion of the track of the second conductive ink overlaps with at least a portion of the track of first conductive ink.

19. The sensor sheet of claim 1, wherein the track of the second conductive ink is electrically coupled to the track of first conductive ink using at least one of conductive glue or conductive tape.

20. The sensor sheet of claim 1, wherein the first conductive ink includes a first amount of silver and the second conductive ink includes a second amount of silver that is different from the first amount.

* * * * *

UNITED STATES PATENT AND TRADEMARK OFFICE
CERTIFICATE OF CORRECTION

PATENT NO. : 12,016,994 B2
APPLICATION NO. : 17/766887
DATED : June 25, 2024
INVENTOR(S) : Allan Kenneth Frazer Grugeon Hunt It is certified that error appears in the above-identified patent and that said Letters Patent is hereby corrected as shown below:

In the Specification

Column 20, Line 51, delete "MM." and insert -- MRI. --.

Signed and Sealed this
Twentieth Day of August, 2024

Katherine Kelly Vidal
*Director of the United States Patent and Trademark Office*